United States Patent [19]
Zinke et al.

[11] Patent Number: 4,544,492
[45] Date of Patent: Oct. 1, 1985

[54] LUBRICANT COMPOSITIONS

[75] Inventors: Horst Zinke, Ernsthofen, Fed. Rep. of Germany; Rolf Schumacher, Marly, Switzerland

[73] Assignee: Ciba-Geigy Corporation, Ardsley, N.Y.

[21] Appl. No.: 605,947

[22] Filed: May 1, 1984

[30] Foreign Application Priority Data

May 9, 1983 [CH] Switzerland ............. 2525/83

[51] Int. Cl.$^4$ ............................................. C10M 1/48
[52] U.S. Cl. ............................. 252/32.7 E; 252/46.7
[58] Field of Search ............. 252/32.7 E, 32.7 R, 252/46.6, 46.7; 260/934, 936, 950

[56] References Cited

U.S. PATENT DOCUMENTS 3,655,556  4/1972  Allen ............................. 252/32.7 E
3,784,588  1/1974  Miles .
4,333,841  6/1982  Schmidt et al. .
4,472,288  9/1984  Frost, Jr. ......................... 252/32.7 E Primary Examiner—Jacqueline V. Howard
Attorney, Agent, or Firm—Luther A. R. Hall

[57] ABSTRACT

Lubricant compositions containing (a) a mineral and/or synthetic base oil and (b) at least one compound of the formula I

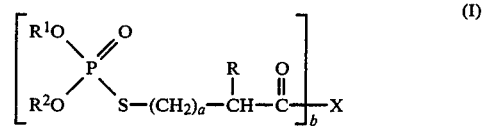

wherein a is 0 or 1, b is 1 to 6, R is H or alkoxycarbonyl, $R^1$ and $R^2$ are independently alkyl, cycloalkyl, aryl, aralkyl or are together substituted alkylene and X is hydroxyl, alkoxy, aryloxy, amino, substituted amino or the residue of a polyol, are described.

5 Claims, No Drawings

LUBRICANT COMPOSITIONS

The present invention relates to lubricant compositions containing monothiophosphoric acid ester derivatives.

Mineral and synthetic lubricants generally have added various additives to improve their end-use properties. There is in particular a need for additives which reduce the coefficient of friction. Such additives must additionally increase the load-bearing capacity of the lubricant, be noncorrosive in respect of the metal components to be protected, and be highly heat-resistant.

Various lubricant additives have already been proposed, examples being the various dithiophosphoric acid derivatives described in German Pat. No. 2,104,041 and German Offenlegungsschrift No. 2,756,488. The properties of such additives in lubricating oils are frequently unsatisfactory. In particular, the friction-reducing action or the thermal resistance is not as high as it should be.

It has now been found that certain ashfree monothiophosphoric acid esters of the formula I have a clearly better friction-reducing action in the mixed friction field at elevated temperatures in mineral and synthetic lubricants than have either the zinc dithiophosphates or the corresponding metalfree dithiophosphates.

The invention accordingly provides lubricant compositions containing (a) a mineral and/or synthetic base oil and (b) at least one compound of the formula I

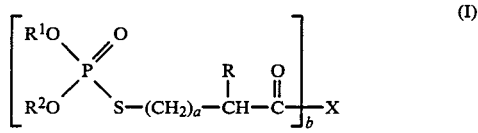

in which a is 0 or 1, b is an integer from 1 to 6, R is —H, —CH$_3$, —COOH, C$_2$–C$_{13}$-alkoxycarbonyl where the alkyl radical can be interrupted by one or two oxygen atoms, or C$_6$–C$_{13}$-cycloalkoxycarbonyl, and R$^1$ and R$^2$, independently of each other, are each C$_3$–C$_{12}$-alkyl which can be interrupted by one or two oxygen or sulfur atoms, C$_5$–C$_{12}$-cycloalkyl, phenyl which is unsubstituted or substituted by one to three C$_1$–C$_{12}$-alkyl groups, or C$_7$–C$_9$-phenylalkyl, and R$^1$ and R$^2$ together can be a bifunctional radical of the formula II

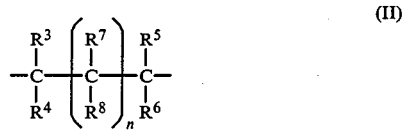

where n is 0 or 1, R$^3$, R$^4$, R$^5$ and R$^6$, independently of each other, are each —H, C$_1$–C$_4$-alkyl, C$_5$–C$_{12}$-cycloalkyl or phenyl, and R$^7$ and R$^8$, independently of each other, are each —H, C$_1$–C$_4$-alkyl, phenyl, —NO$_2$, C$_2$–C$_{19}$-alkoxycarbonyl or C$_6$–C$_{13}$-cycloalkoxycarbonyl, or R$^7$ and R$^8$, together with the carbon atom to which they are bonded, are a cyclopentenyl or cyclohexenyl ring, X, if b=1, is —OR$^9$ or —N(R$^{10}$)(R$^{11}$), where R$^9$ is —H, C$_1$–C$_{22}$-alkyl, C$_5$–C$_{12}$-cycloalkyl or phenyl, and R$^{10}$ and R$^{11}$, independently of each other, are each —H, C$_1$–C$_{22}$-alkyl which is unsubstituted or interrupted by one or two oxygen atoms, C$_2$–C$_{22}$-alkenyl or C$_5$–C$_{12}$-cycloalkyl, or R$^{10}$ and R$^{11}$, together with the nitrogen atom to which they are bonded, are a C$_2$–C$_{22}$-alkylene or C$_2$–C$_{22}$-alkenylene ring which can be interrupted by oxygen, sulfur and/or nitrogen atoms, and X, if b>1, is a polyvalent radical of the formulae —OC$_m$H$_{2m}$O—, where the C$_m$H$_{2m}$ group can be interrupted by 1 or 2 oxygen or sulfur atoms, —OCH$_2$—C(R$^{12}$)(R$^{13}$)—CH$_2$O—,

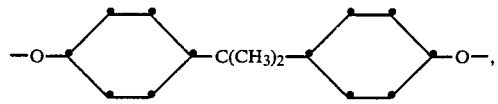

(—OCH$_2$)$_3$C—R$^{14}$, (—OCH$_2$)$_4$C or (—OCH$_2$)$_3$C—CH$_2$—O—CH$_2$—C(CH$_2$O—)$_3$, where m is an integer from 2 to 40, and R$^{12}$ and R$^{13}$ are each C$_1$–C$_4$-alkyl, C$_2$–C$_9$-alkoxycarbonyl, C$_6$–C$_{13}$-cycloalkoxycarbonyl, phenyl or —NO$_2$, or R$^{12}$ and R$^{13}$, together with the carbon atom to which they are bonded, are a cyclopentenyl ring, and R$^{14}$ is —CH$_3$ or —C$_2$H$_5$.

R$^1$ to R$^{13}$ can be straight-chain or branched alkyl, for example, in the case of R$^3$ to R$^{13}$, methyl, ethyl, n-propyl, isopropyl, n-butyl, sec.-butyl and tert.-butyl, in the case of R$^9$ in the —OR$^9$ radical and R$^{10}$ and R$^{11}$, in addition n-pentyl, tert.-pentyl, n-hexyl, 1- and 6-methylpentyl, n-octyl, 2-ethylhexyl, 1,1-dimethylhexyl, n-decyl, n-dodecyl, 2-ethyldecyl, 1,1,7,7-tetramethyloctyl, n-tetradecyl, n-hexadecyl, n-octadecyl and eicosyl, but in particular, in the case of R$^9$, C$_1$–C$_{13}$-alkyl.

C$_3$–C$_{12}$-alkyl radicals R$^1$ and R$^2$ can be the same radicals which have already been mentioned as having 3 to 12 C atoms.

In the case of R$^1$ and R$^2$ being alkyl substituted by one or two oxygen or sulfur atoms, they can be, for example, alkoxyalkyl and alkylthioalkyl groups, in particular alkoxyalkyl having a total of 3–12 C atoms, such as 2-methoxyethyl, 2-ethoxyethyl, 2-n-propoxyethyl, 2-isopropoxyethyl, 2-n-butoxyethyl, 2-n-octoxyethyl and methoxypropyl, as well as diethylene glycol monoalkyl ether groups such as β-methoxyethoxyethyl, β-ethoxyethoxyethyl and β-n-butyloxyethoxyethyl. A particular mention should go to compounds in which R$^1$ and R$^2$ are each alkoxyalkyl having 3–6 C atoms. In the case of R$^{10}$ and R$^{11}$ being alkyl interrupted by one or two oxygen atoms, they can be the same radicals as have already been mentioned.

C$_5$–C$_{12}$-cycloalkyls R$^1$, R$^2$, R$^3$ to R$^6$, R$^{10}$ and R$^{11}$ can be for example cyclopentyl, cyclohexyl, monomethylcyclohexyl, dimethylcyclohexyl, cyclooctyl, cyclodecyl or cyclododecyl. Cyclohexyl is preferred.

A C$_5$–C$_{12}$-cycloalkyl R$^9$ can be one of the radicals already mentioned, but in particular C$_6$–C$_9$-cycloalkyl.

C$_2$–C$_{22}$-alkenyls R$^{10}$ and R$^{11}$ can be straight-chain or branched substituents having one or more double bonds, preferably one or two, for example 2-butenylene, 3-butenylene, 4-butenylene, 2-pentenylene, 3-pentenylene or 4-pentenylene.

In the case of R$^1$ and R$^2$ being phenyl substituted by one to three alkyl groups they can be for example methyl, ethyl, isopropyl, n-butyl, sec.-butyl, tert.-butyl, tert.-pentyl, n-hexyl, n-octyl, 1,1,3,3-tetramethylbutyl or 1,1,3,3,5,5-hexamethylhexyl groups.

C$_7$–C$_9$-phenylalkyls R$^1$ and R$^2$ can be α,α-dimethylbenzyl, β-phenylethyl and in particular benzyl. C$_2$–C$_{19}$-alkoxycarbonyls R$^7$ and R$^8$ can be for example methoxycarbonyl, ethoxycarbonyl, butoxycarbonyl, hexoxycarbonyl, octoxycarbonyl, dodecyloxycarbonyl or octyldecyloxycarbonyl. Preferred alkoxycarbonyl groups contain 2 to 9 C atoms, but in particular 2 to 5 C atoms.

$C_2$–$C_{13}$- or $C_2$–$C_9$-alkoxycarbonyls R, $R^{12}$ and $R^{13}$ can be the same radicals as have already been mentioned as having 2 to 13 C or 2 to 9 C atoms respectively. $C_2$–$C_5$-alkoxycarbonyl is preferred. $C_6$–$C_{13}$-cycloalkoxycarbonyls R, $R^7$, $R^8$, $R^{12}$ and $R^{13}$ can be for example cyclopentoxy, cyclohexoxy, trimethylcyclohexoxy or cycloheptoxycarbonyl, but in particular cyclohexoxycarbonyl.

An —$OC_mH_{2m}O$— X contains as $C_mH_{2m}$ radical for example ethylene, 1,2-propylene, 3-methyl-1,3-propylene, 1,4-butylene, 1,5-pentylene, 1,6-hexamethylene, 2-methylethylene, 2-ethylethylene, 2-eicosylethylene, 1,2-dimethylethylene, 1,1,2,2-tetramethylethylene, 3-methyl-1,3-pentylene or 3-tert.-butyl-1,3-pentylene. An —$OC_mH_{2m}O$— radical which is interrupted by oxygen or sulfur atoms can be for example [—O—CH(CH$_3$)—CH$_2$—$_2$O, [—O—CH(CH$_3$)—CH$_2$—$_2$S or —OC$_2$H$_4$OC$_2$H$_4$O—.

$R^7$ and $R^8$, together with the C atom to which they are bonded, can be for example 2- or 3-cyclopenten-1-yl or 3-cyclohexen-1-yl.

$R^{10}$ and $R^{11}$ in the form of $C_2$–$C_{22}$-alkylene or $C_2$–$C_{22}$-alkenylene are, together with the N atom to which they are bonded, a ring which can be interrupted by one or more atoms from the group comprising oxygen, sulfur and nitrogen. The alkylene or alkenylene portion of this ring can be monosubstituted or polysubstituted by $C_1$–$C_4$-alkyl, such as $C_1$–$C_4$-alkylated 1,4-butylene or 1,5-pentylene, in particular methylated 1,4-butylene or 1,5-pentylene. The alkenylene portion of the ring can have one or two double bonds and be for example 2-butenylene, 3-butenylene, 4-butenylene, 2-pentenylene, 3-pentenylene or 4-pentenylene. Such a heterocyclic ring which is also interrupted by additional O, S and/or N atoms can be, together with the N atom linking $R^{10}$ and $R^{11}$, in particular morpholino, thiomorpholino, piperazino, 4-methylpiperazino, pyrazole, imidazole, 1,2,3-triazole, 1,2,4-triazole, tetrazole, 2-imidazoline, 4-imidazoline, 2H,6H-1,5,2-dithiazine, pyraline, 3-pyrazoline or 2-pyrazoline.

Preferred lubricant compositions contain at least one compound of the formula I in which a is 0, b is an integer from 1 to 4, R is —H or $C_2$–$C_5$-alkoxycarbonyl, and $R^1$ and $R^2$, independently of each other, are each $C_3$–$C_{12}$-alkyl which can be interrupted by one or two oxygen atoms, cyclohexyl, phenyl which is unsubstituted or substituted by one to three $C_1$–$C_{12}$-alkyl groups, or benzyl, or $R^1$ and $R^2$ together can be a bifunctional radical of the formula II $$\begin{array}{c} R^3 \\ | \\ -C- \\ | \\ R^4 \end{array} \left( \begin{array}{c} R^7 \\ | \\ -C- \\ | \\ R^8 \end{array} \right)_n \begin{array}{c} R^5 \\ | \\ -C- \\ | \\ R^6 \end{array} \quad (II)$$

where n is 0 or 1, $R^3$, $R^4$, $R^5$ and $R^6$, independently of each other, are each —H, —CH$_3$ or —C$_2$H$_5$, $R^7$ and $R^8$, independently of each other, are each —H, $C_1$–$C_4$-alkyl, phenyl, —NO$_2$ or $C_2$–$C_9$-alkoxycarbonyl, or $R^7$ and $R^8$, together with the carbon atom to which they are bonded, are a cyclohexenyl ring, and X, if b=1, is —OR$^9$ or —N(R$^{10}$)R$^{11}$) where $R^9$ is —H, $C_1$–$C_{13}$-alkyl or $C_6$–$C_9$-cycloalkyl, and $R^{10}$ and $R^{11}$ are each —H, or $R^{10}$ and $R^{11}$, together with the nitrogen atom to which they are bonded, are a $C_4$–$C_6$-alkylene ring which can be interrupted by oxygen, sulfur or nitrogen atoms, and X, if b>1, is a polyvalent radical of the formula —$OC_mH_{2m}O$— where the $C_mH_{2m}$ group can be interrupted by one or two oxygen or sulfur atoms and m is a number from 4 to 6, or X is —OCH$_2$—C($R^{12}$)($R^{13}$)—CH$_2$O—, (—OCH$_2$)$_3$C—$R^{14}$ or (—OCH$_2$)$_4$C, where $R^{12}$ and $R^{13}$ are each $C_1$–$C_4$-alkyl or $C_2$–$C_4$-alkoxycarbonyl, or $R^{12}$ and $R^{13}$, together with the carbon atom to which they are bonded, are a cyclopentenyl ring, and $R^{14}$ is —CH$_3$ or —C$_2$H$_5$.

Particularly preferred lubricant compositions contain at least one compound of the formula I in which a and b are as defined above, R is —H, and $R^1$ and $R^2$, independently of each other, are each $C_3$–$C_{12}$-alkyl, cyclohexyl or phenyl which is unsubstituted or substituted by 1 to three $C_1$–$C_{12}$-alkyl groups, or $R^1$ and $R^2$ together are a bifunctional radical of the formula II where n is 1, $R^3$, $R^4$, $R^5$ and $R^6$ are each —H and $R^7$ and $R^8$ are each $C_1$–$C_4$-alkyl or $C_2$–$C_3$-alkoxycarbonyl, and X, if b=1, is —OR$^9$ or —N(R$^{10}$)(R$^{11}$) where $R^9$ is —H, $C_1$–$C_{13}$-alkyl or $C_6$–$C_9$-cyclohexyl and $R^{10}$ and $R^{11}$ are each —H, or $R^{10}$ and $R^{11}$, together with the nitrogen atom to which they are bonded, are morpholino, thiomorpholino, piperazino or 4-methylpiperazino, and X, if b>1, is a polyvalent radical of the formulae —$OC_mH_{2m}O$—, (—O—$C_2H_4$)$_2$O or (—OCH$_2$)$_4$C, where m is an integer from 4 to 6.

In likewise preferred compounds of the formula I, X, if b=1, is —OR$^9$ and X, if b>1, is a polyvalent radical of the formulae —$OC_mH_{2m}O$—, —OCH$_2$—C($R^{12}$)($R^{13}$)—CH$_2$O—,

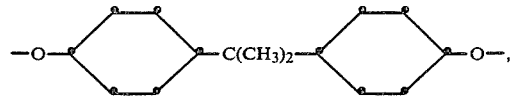

(—OCH$_2$)$_3$C—$R^{14}$, (—OCH$_2$)$_4$C or (—OCH$_2$)$_3$C—CH$_2$—O—CH$_2$—C(CH$_2$O—)$_3$, and $R^9$, $R^{12}$, $R^{13}$, $R^{14}$ and m are as defined on pages 2 and 3. b is preferably 1.

In non-limiting examples of compounds of the formula I the symbols are defined as follows:

| $R^1$ | $R^2$ | a | R | b | X |
|---|---|---|---|---|---|
| 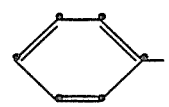 | 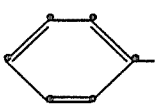 | 1 | —H | 1 | —OC$_2$H$_5$ |

-continued

| R¹ | R² | a | R | b | X |
|---|---|---|---|---|---|
| —C₃H₇(i) | —C₃H₇(i) | 1 | —H | 1 | —OC₂H₅ |
| —C₃H₇(i) | —C₃H₇(i) | 1 | —H | 2 | —OCH₂CH₂O— |
| —C₈H₁₇(i) | —C₈H₁₇(i) | 1 | —H | 1 | —NH₂ |
| | (CH₃)(CH₃)C(CH₂—)(CH₂—) | 1 | —CH₃ | 1 | —OC₂H₅ |
| cyclohexyl | cyclohexyl | 1 | —H | 1 | —O—C₄H₉(n) |
| C₆H₅—CH₂— | C₆H₅—CH₂— | 1 | —COOC₂H₅ | 1 | —OC₂H₅ |
| C₆H₅—(CH₂)₃— | C₆H₅—(CH₂)₃— | 0 | —H | 1 | —O—C₆H₁₃(n) |
| H₅C₂OC₂H₄— | H₅C₂OC₂H₄— | 0 | —H | 1 | —O—C₈H₁₇(n) |
| H₅C₂SC₂H₄— | H₅C₂SC₂H₄— | 0 | —H | 1 | —N(morpholino) |
| —C₃H₇(i) | —C₃H₇(i) | 0 | —H | 1 | —N(morpholino) |
| H₁₉C₉—C₆H₄— | H₁₉C₉—C₆H₄— | 0 | —H | 1 | —OC₂H₅ |
| —C₈H₁₇(n) | —C₈H₁₇(n) | 0 | —H | 1 | —O—(2,2,6-trimethyl ring) |
| | (H₅C₂)(n-H₉C₄)C(—)(—) | 0 | —COOC₂H₅ | 1 | —OC₂H₅ |
| —C₄H₉(i) | —C₄H₉(i) | 0 | —H | 1 | —OC₂H₅ |
| | (H₃C)(n-H₇C₃)C(—)(—) | 0 | —H | 2 | —OC₂H₄—S—C₂H₄O— |
| | (O₂N)(H₃C)C(—)(—) | 0 | —H | 1 | —OC₄H₉(t) |
| —C₁₂H₂₅(n) | —C₁₂H₂₅(n) | 0 | —H | 1 | —OC₂H₅ |

-continued

| R¹ | R² | a | R | b | X |
|---|---|---|---|---|---|
| —C₃H₇(n) | —C₃H₇(n) | 0 | —H | 2 | (H₃C)₂C(—⟨ring⟩—O—)₂ |
| —C₄H₉(i) | —C₄H₉(i) | 0 | —H | 3 | H₅C₂\\C/CH₂O—, —O—CH₂/ \\CH₂O— |
| (H₃C)₃C—⟨ring with C(CH₃)₃⟩ | (H₃C)₃C—⟨ring with C(CH₃)₃⟩ | 0 | —H | 1 | —N(—⟨ring⟩—)₂ |
| —C₅H₁₁(n) | —C₅H₁₁(n) | 0 | —H | 1 | —N⟨ring⟩ |
| —C₆H₁₃(n) | —C₆H₁₃(n) | 0 | —H | 1 | —O—⟨ring⟩ |

A number of compounds of the formula I are known products. They are prepared by methods known per se, for example by the general methods described in "Houben-Weyl, Methoden der organischen Chemie" [Houben-Weyl, Methods of Organic Chemistry], Volume 12, part 2, pages 652–681, (published by Thieme, 1964).

Appropriate alcohols or diols are reacted with PCl₃ to prepare, either directly or via a subsequent reaction between water and the chlorophosphites which have been isolated beforehand, first of all the respective open-chain or cyclic diphosphites of the formula III

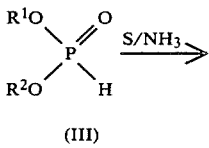

(III)

which are reacted with sulfur/NH₃ in an inert organic solvent to give, via the readily accessible corresponding ammonium monothiophosphates of the formula IV and through subsequent reaction with a suitable halogen compound, the monothiophosphoric acid esters of the formula I. The following reaction diagram illustrates the reaction for the case b=1:

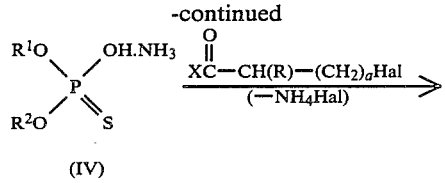

(IV)

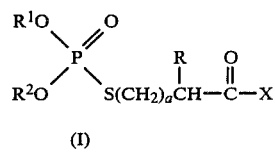

(I)

In the formulae I, III and IV, R, R¹, R², X and a are as defined above, Hal is halogen and is preferably chlorine or bromine.

The reaction of 1,3-diols can advantageously also take the form of direct esterification of the diols with H₃PO₃ (phosphorous acid) to give the corresponding compounds of the formula III.

Other compounds of the formula I are novel and therefore also comprise part of the subject-matter of the invention. They are prepared using methods which are analogous to those given for the known compounds. Novel intermediates of the formulae III and IV therefore also comprise part of the subject-matter of the present invention.

The compounds of the formula I can be used in the crude state, i.e. the state in which they are obtained at the end of their synthesis. They can also be purified before they are used as lubricant additives.

If more than one compound of the formula I are used simultaneously in accordance with the invention, these compounds are admixed to the base oil either singly or mixed.

The compounds of the formula I act as high-pressure additives in lubricants even if present in only very small amounts. For instance, mineral and synthetic lubricating oils, as well as mixtures thereof, to which 0.05 to 5% by weight, based on the lubricant, and preferably 0.1 to 3% by weight of compound of the formula I have been added, have excellent high-pressure lubricating properties. Thus, the lubricant compositions according to the invention are distinguished in particular by a good load-bearing capacity, good wear-prevention properties, and a good friction-reducing action. These ashfree compounds are additionally highly heat-resistant.

The possible lubricants will be familiar to those skilled in the art and are described, for example, in "Schmiermittel Taschenbuch" [Lubricants Handbook] (published by Hüthig, Heidelberg, 1974).

The lubricating oil formulation can additionally contain further additives which are added with the intention of improving certain end-use properties. They are preferably antioxidants, metal passivators, rust inhibitors, viscosity index improvers, setting point reducers, dispersants/detergents, thickeners and various known wear-prevention agents, high-pressure agents and friction reducers.

The level of these additives in the lubricant compositions is not restricted. It depends on the chemical structure of the additives and on the field of application and is known to those skilled in the art. Preferably, a number of such additives are combined in order to obtain the most suitable properties.

Examples of antioxidants are:

(a) alkylated and non-alkylated aromatic amines and mixtures thereof, for example dioctyldiphenylamine, mono-t-octylphenyl-$\alpha$- and -$\beta$-naphthylamines, phenothiazine, dioctylphenothiazine, phenyl-$\alpha$-naphthylamine, N,N'-di-sec.-butyl-p-phenylenediamine;

(b) sterically hindered phenols, for example 2,6-di-tert.-butyl-p-cresol, 4,4'-bis-(2,6-diisopropylphenol), 2,4,6-triisopropylphenol, 2,2'-thio-bis-(4-methyl-6-tert.-butylphenol), 4,4'-methylene-bis-(2,6-di-tert.-butylphenol);

(c) alkyl, aryl or alkaryl phosphites, for example trinonyl phosphite, triphenyl phosphite, diphenyldecyl phosphite;

(d) esters of thiodipropionic acid or thiodiacetic acid, for example dilauryl thiodipropionate or dioctyl thiodiacetate;

(e) salts of carbamic and dithiophosphoric acids, for example antimony diamyldithiocarbamate, zinc diamyldithiophosphate;

(f) combination of two or more antioxidants from among the above additives, for example an alkylated amine and a sterically hindered phenol.

Examples of metal passivators are:

(a) for copper, for example benzotriazole, tetrahydrobenzotriazole, 2-mercaptobenzotriazole, 2,5-dimercaptothiadiazole, salicylidenepropylenediamine, salts of salicylaminoguanidine;

(b) for lead, for example sebacic acid derivatives, quinizarin, propyl gallate;

(c) combination of two or more of the above additives.

Examples of rust inhibitors are:

(a) organic acids, their esters, metal salts and anhydrides, for example N-oleoylsarcosine, sorbitan monooleate, lead naphthenate, dodecylsuccinic anhydride;

(b) nitrogen-containing compounds, for example I. primary, secondary or tertiary aliphatic or cycloaliphatic amines and amine salts of organic and inorganic acids, for example oil-soluble alkylammonium carboxylates; II. heterocyclic compounds, for example substituted imidazolines and oxazolines;

(c) phosphorus-containing compounds, for example amine salts of partial esters of phosphoric acid;

(d) sulfur-containing compounds, for example barium dinonylnaphthalenesulfonates, calcium petroleumsulfonates;

(e) combinations of two or more of the above additives.

Examples of viscosity index improvers are: polymethacrylates, vinylpyrrolidone/methacrylate copolymers, polybutenes, olefin copolymers, styrene/acrylate copolymers.

Examples of setting point reducers are: alkylated naphthalenes, alkylated phenols, polymethacrylates.

Examples of detergents and dispersants are: polyalkenylsuccinimides, oil-soluble metal soaps, such as Ca, Ba, Mg and Al carboxylates, phenylates or sulfonates.

Examples of other wear-prevention additives are: sulfur- and/or phosphorus- and/or halogen-containing compounds, such as sulfurised vegetable oils, zinc dialkyl dithiophosphates, tritolyl phosphate, chlorinated paraffins, alkyl and aryl disulfides.

The subject-matter of the invention also includes the use of compounds of the formula I as lubricant-additives in lubricants, in particular in lubricating oils and greases.

The compounds of the formula I which form part of the subject-matter of the invention are distinguished in particular by good lubricating properties in the mixed friction field at elevated temperatures. They are also highly heat-resistant and ashfree.

The lubricant compositions according to the invention are used in particular in hydraulic oils, gear and engine oils, lubricating greases and metal-machining oils.

The following examples illustrate the invention. Parts and percentages therein are by weight.

EXAMPLE 1

O,O-Dicyclohexyl thiophosphate (ammonium salt)

25.65 parts (0.8 mole) of sulfur are added to a solution of 197 parts (0.8 mole) of dicyclohexyl phosphite in 800 ml of isopropanol, and a moderately fast stream of ammonia is passed in with stirring, during which the temperature is held at about 25° C. by cooling with ice. When all the sulfur has gone into solution, the supply of $NH_3$ is interrupted, and the mixture is then stirred at room temperature for one hour and at 40° C. for one hour. After addition of 6 parts of active charcoal the mixture is clarified by filtration, and the solvent is distilled in vacuo until the ammonium salt starts to precipitate. The precipitated crystals are filtered off with suction, washed with petroleum ether, and dried in vacuo at 80° C. This produces 191.9 parts (81% of theory) of O,O-dicyclohexyl thiophosphate in the form of colourless crystals having a melting point of 177°–180° C. (as ammonium salt).

| Combustion analysis: | % N | % P | % S |
|---|---|---|---|
| calculated: | 4.74 | 10.49 | 10.86 |
| found: | 4.8 | 10.6 | 10.7 |
| $^{31}$P-NMR analysis (in ppm based on $H_3PO_4$): +55.1 ppm. | | | |

The monothiophosphate ammonium salts given in Table 1 are prepared analogously:

diisopropyl-S-(n-hexyl acetate)-thiophosphoric acid as a colourless liquid. The product thus isolated is further purified by molecular distillation at 60° C./6.65×10⁻³-1.33×10⁻² mbar. Yield: 91.8 parts (77% of theory) of a colourless liquid having a refractive index ($n_D^{20}$) of 1.4580. $^{31}$P-NMR analysis: 22.8 ppm/H$_3$PO$_4$

TABLE 1

$$(RO)_2\overset{\overset{S}{\|}}{P}-OH \cdot NH_3$$

| Example No. | R | Yield (% of theory) | Melting point | $^{31}$P—NMR ppm/H$_3$PO$_4$ | Analysis: calculated found [% P] | [% S] |
|---|---|---|---|---|---|---|
| 2 | n-C$_8$H$_{17}$— | 67% | 170–180° C. | +57.7 | 8.71<br>8.7 | 9.02<br>9.1 |
| 3 | C$_6$H$_5$— | 97% | 108–113° C. | +46.8 | 10.93<br>10.5 | 11.32<br>11.1 |
| 4 | n-C$_4$H$_9$— | 83% | 155–160° C. | +57.7 | 12.73<br>12.8 | 13.18<br>12.9 |
| 5 | n-C$_3$H$_7$— | 91% | 151–155° C. | +58.2 | 14.39<br>14.7 | 14.89<br>15.1 |
| 6 | i-C$_3$H$_7$— | 84% | 178–179° C. | +53.6 | 14.39<br>14.5 | 14.89<br>15.3 |
| 7 | 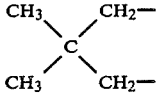 | 98% | 225–226° C.* | +55.3 | 15.55<br>15.4 | 16.1<br>16.0 |

*After recrystallisation from petroleum ether/isopropanol

EXAMPLE 8

O,O-Diisopropyl-S-(n-hexyl acetate)-thiophosphoric acid

A mixture of 75.36 parts (0.35 mole) of ammonium O,O-diisopropylthiophosphate (Example 6) and 62.55 parts (0.35 mole) of n-hexyl chloroacetate in 600 ml of toluene is heated to 90° C. in the course of one hour and is stirred at this temperature for 12 hours. The precipitated ammonium chloride is then filtered off, and the organic phase of the filtrate is washed with water/sodium hydrogen carbonate and then with water. After drying the solution with anhydrous sodium sulfate the solvent is distilled off in vacuo and the residue is distilled off in an oil pump vacuum at 60° C./6.65×10⁻² mbar, producing 113.75 parts (96% of theory) of O,O-

| Combustion analysis: | % C | % H | % P | % S |
|---|---|---|---|---|
| calculated: | 49.40 | 8.59 | 9.10 | 9.42 |
| found: | 49.37 | 8.43 | 9.12 | 9.49 |

The monothiophosphate esters of the formula I given in Table 2 are prepared analogously, except for Example 10 which is prepared using methods known per se, by addition of O,O-diisopropyl thiophosphate onto ethyl acrylate.

TABLE 2

| Example No. | Monothiophosphoric acid esters of the formula I | | | | | | Refractive index $n_D^{20}$ | Analysis: % P calcul.: found: | $^{31}$P—NMR, in ppm/H$_3$PO$_4$ |
|---|---|---|---|---|---|---|---|---|---|
| | R$^1$ | R$^2$ | a | R | b | X | | | |
| 9 | n-C$_6$H$_{13}$— | n-C$_6$H$_{13}$— | 0 | H— | 1 | n-C$_6$H$_{13}$—O— | 1.4625 | 7.3<br>7.4 | +25.7 |
| 10+ | i-C$_3$H$_7$— | i-C$_3$H$_7$— | 1 | H— | 1 | C$_2$H$_5$O— | 1.4591 | 10.4<br>10.4 | +24.3 |
| 11 | i-C$_3$H$_7$— | i-C$_3$H$_7$— | 0 | H— | 1 | HO— | 1.4681 | 12.1<br>11.9 | +23.8 |
| 12 | i-C$_3$H$_7$— | i-C$_3$H$_7$— | 0 | H$_5$C$_2$O$_2$C— | 1 | C$_2$H$_5$O— | 1.4542 | 8.7<br>8.3 | +20.6 |
| 13 | i-C$_8$H$_{17}$— | i-C$_8$H$_{17}$— | 0 | H— | 1 | H$_2$N— | 1.4801 | 7.8<br>7.8 | — |
| 14 | i-C$_8$H$_{17}$— | i-C$_8$H$_{17}$— | 0 | H— | 1 | C$_2$H$_5$O— | 1.4640 | 7.3<br>7.4 | +25.7 |
| 15 | i-C$_8$H$_{17}$— | i-C$_8$H$_{17}$— | 0 | H— | 1 | t-C$_4$H$_9$—O— | 1.4607 | 6.8<br>7.0 | +26.0 |
| 16 | n-C$_{12}$H$_{25}$— | n-C$_{12}$H$_{25}$— | 0 | H— | 1 | CH$_3$O— | 1.4663 | 5.9<br>5.5 | +25.3 |
| 17 | (CH$_3$)$_2$C(CH$_2$—)$_2$ | | 0 | H— | 1 | n-C$_6$H$_{13}$—O— | 1.4823 | 9.6<br>9.4 | +17.6 |
| 18 | furyl | furyl | 0 | H— | 1 | i-C$_8$H$_{17}$O— | 1.5277 | 7.1<br>6.9 | +18.5 |

TABLE 2-continued

| Example No. | Monothiophosphoric acid esters of the formula I | | | | | Refractive index $n_D^{20}$ | Analysis: % P calcul.: found: | $^{31}$P—NMR, in ppm/H$_3$PO$_4$ |
|---|---|---|---|---|---|---|---|---|
| | R$^1$ | R$^2$ | a | R | b | X | | |
| 19 | phenyl | phenyl | 0 | H— | 1 | 2,2,6-trimethyl-cyclohexyl-O— | 1.5386 | 6.9 / 6.7 | +18.7 |
| 20 | C$_9$H$_{19}$-phenyl | C$_9$H$_{19}$-phenyl | 0 | H— | 1 | C$_2$H$_5$O— | 1.5217 | 5.1 / 4.7 | +18.6 |
| 21 | cyclohexyl | cyclohexyl | 0 | H— | 1 | n-C$_6$H$_{13}$—O— | 1.4896 | 7.4 / 7.4 | +23.0 |
| 22 | n-C$_4$H$_9$— | n-C$_4$H$_9$— | 0 | H— | 4 | C(CH$_2$—O—)$_4$ | 1.4861 | 10.3 / 10.1 | +25.2 |
| 23 | i-C$_8$H$_{17}$— | i-C$_8$H$_{17}$— | 0 | H— | 4 | C(CH$_2$—O—)$_4$ | 1.4808 | 7.5 / 7.5 | +25.2 |
| 24 | phenyl | phenyl | 0 | H— | 1 | n-C$_6$H$_{13}$O— | 1.5373 | 7.6 / 7.6 | +19.5 |
| 25 | i-C$_8$H$_{17}$— | i-C$_8$H$_{17}$— | 0 | H— | 1 | morpholino (O,N-ring) | 1.4870 | 6.7 / 6.6 | +26.1 |
| 26 | n-C$_3$H$_7$— | n-C$_3$H$_7$— | 0 | H— | 1 | n-C$_6$H$_{13}$— | 1.4604 | 9.1 / 9.2 | +25.3 |

USE EXAMPLES

EXAMPLE 30

To test the friction-reducing properties the compounds given below are incorporated into a non-alloyed lubricating oil (viscosity: 139.3 mm$^2$·sec$^{-1}$/40° C.), and the coefficient of friction is determined at 40° C. and 110° C. by means of an SRV tester (Schwing-Reib-Verschleiss [Vibration-Friction-Wear] tester supplied by the Munich firm of Optimol, see Lubrication Engineering, Vol. 39, No. 11, November 1982, Advertising Index, cover 3, page 729).

In the friction tester used a vibrating sphere (50 Hz) is pressed with a force of 200N against a firmly clamped metal platelet on which there is the oil under test.

Horizontal and vertical forces are measured by means of a piezoelectric pick-up, and the resulting signal is passed through a load amplifier and directly registered on a recorder.

The test results are given in the table below.

TABLE 3

(Measurements of coefficient of friction)

| Test No. | Additive 4 as per Example No. | Test concentration* in % | Coefficient of friction μ | |
|---|---|---|---|---|
| | | | 40° C. | 110° C. |
| 1 | none | | 0.148 | 0.111 |
| 2 | 8 | 1.92 | 0.077 | 0.075 |
| 3 | 9 | 2.39 | | 0.070 |
| 4 | 17 | 1.83 | —** | 0.072 |
| 5 | 24 | 2.30 | 0.080 | 0.066 |
| 6 | 26 | 1.92 | | 0.054 |

*Test concentration corresponds to a P content of 0.174%, i.e. the additive concentration was purposely chosen to be such that the measurements were carried out with the phosphorus concentration the same for all the additives.
**Not sufficiently soluble at 40° C.

The monothiophosphoric acid esters of the formula I which are the subject-matter of the invention, compared with a base oil which contains no additive, have a superior friction-reducing action in the mixed friction field not only at low (40° C.) but also at elevated (110° C.) temperatures.

We claim:

1. A lubricant composition which comprises
(a) a mineral oil, a synthetic oil or a mixture of said oils, and
(b) 0.05 to 5% by weight, based on component (a), of at least one compound of formula I

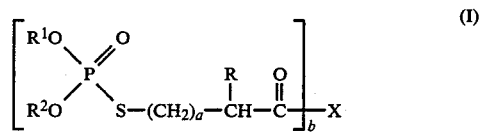
(I)

in which a is 0 or 1, b is an integer from 1 to 6, R is —H, —CH$_3$, —COOH, C$_2$-C$_{13}$-alkoxycarbonyl where the alkyl radical can be interrupted by one or two oxygen atoms, or is $C_6$-$C_{13}$-cycloalkoxycarbonyl; $R^1$ and $R^2$, independently of each other, are each $C_3$-$C_{12}$-alkyl which can be interrupted by one or two oxygen or sulfur atoms, $C_5$-$C_{12}$-cycloalkyl, phenyl, phenyl substituted by one to three $C_1$-$C_{12}$-alkyl groups; or $C_7$-$C_9$-phenylalkyl; or $R^1$ and $R^2$ together can be a bifunctional radical of the formula II

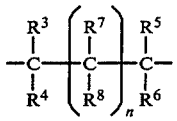
(II)

where n is 0 or 1, $R^3$, $R^4$, $R^5$ and $R^6$, independently of each other, are each —H, $C_1$-$C_4$-alkyl, $C_5$-$C_{12}$-cycloalkyl or phenyl, and $R^7$ and $R^8$, independently of each other, are each —H, $C_1$-$C_4$-alkyl, phenyl, —$NO_2$, $C_2$-$C_{19}$-alkoxycarbonyl or $C_6$-$C_{13}$-cycloalkoxycarbonyl, or $R^7$ and $R^8$, together with the carbon atom to which they are bonded, are a cyclopentenyl or cyclohexenyl ring, and when b is 1, X is —$OR^9$ or —$N(R^{10})(R^{11})$, where $R^9$ is —H, $C_1$-$C_{22}$-alkyl, $C_5$-$C_{12}$-cycloalkyl or phenyl, $R^{10}$ and $R^{11}$, independently of each other, are each —H, $C_1$-$C_{22}$-alkyl, said alkyl interrupted by one or two oxygen atoms, $C_2$-$C_{22}$-alkenyl or $C_5$-$C_{12}$-cycloalkyl; or $R^{10}$ and $R^{11}$, together with the nitrogen atom to which they are bonded, are a $C_2$-$C_{22}$-alkylene or $C_2$-$C_{22}$-alkenylene ring which can be interrupted by oxygen, sulfur and/or nitrogen atoms, or when b>1, X is a polyvalent radical of the formulae —$OC_mH_{2m}O$—, where the $C_mH_{2m}$ group can be interrupted by one or two oxygen or sulfur atoms, —$OCH_2$—$C(R^{12})(R^{13})$—$CH_2O$—,

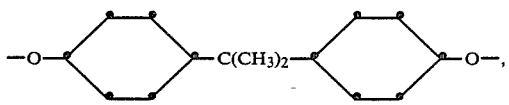

(—$OCH_2)_3C$—$R^{14}$, (—$OCH_2)_4C$ (—$OCH_2)_3C$—$CH_2$—$O$—$CH_2$—$C(CH_2O$—$)_3$, where m is an integer from 2 to 40, and $R^{12}$ and $R^{13}$ are each $C_1$-$C_4$-alkyl, $C_2$-$C_9$-alkoxycarbonyl, $C_6$-$C_{13}$-cycloalkoxycarbonyl, phenyl or —$NO_2$, or $R^{12}$ and $R^{13}$, together with the carbon atom to which they are bonded, are a cyclopentenyl ring, and $R^{14}$ is —$CH_3$ or —$C_2H_5$.

2. A lubricant composition according to claim 1, where in the compound of formula I, a is O, b is an integer from 1 to 4, R is —H or $C_2$-$C_5$-alkoxycarbonyl, $R^1$ and $R^2$, independently of each other, are each $C_3$-$C_{12}$-alkyl which can be interrupted by one or two oxygen atoms, cyclohexyl, phenyl, phenyl substituted by one to three $C_1$-$C_{12}$-alkyl groups; or benzyl, or $R^1$ and $R^2$ together can be a bifunctional radical of the formula II

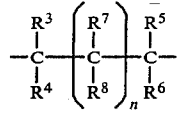
(II)

>here n is 0 or 1, $R^3$, $R^4$, $R^5$ and $R^6$, independently of each other, are each —H, —$CH_3$ or —$C_2H_5$, $R^7$ and $R^8$, independently of each other, are each —H, $C_1$-$C_4$-alkyl, phenyl, —$NO_2$ or $C_2$-$C_9$-alkoxycarbonyl, or $R^7$ and $R^8$, together with the carbon atom to which they are bonded, are a cyclohexenyl ring, and when b is 1, X is —$OR^9$ or —$N(R^{10})(R^{11})$ where $R^9$ is —H, $C_1$-$C_{13}$-alkyl or $C_6$-$C_9$-cycloalkyl and $R^{10}$ and $R^{11}$ are each —H, or $R^{10}$ and $R^{11}$, together with the nitrogen atom to which they are bonded, are a $C_4$-$C_6$-alkylene ring which can be interrupted by oxygen, sulfur or nitrogen atoms, or when b>1, X is a polyvalent radical of the formula —$OC_mH_{2m}O$— where the $C_mH_{2m}$ group can be interrupted by one or two oxygen or sulfur atoms and m is a number from 4 to 6, or X is —$OCH_2$—$C(R^{12})(R^{13})$—$CH_2O$—, (—$OCH_2)_3C$—$R^{14}$ or (—$OCH_2)_4C$, where $R^{12}$ and $R^{13}$ are each $C_1$-$C_4$-alkyl or $C_2$-$C_4$-alkoxycarbonyl, or $R^{12}$ and $R^{13}$, together with the carbon atom to which they are bonded, are a cyclopentenyl ring, and $R^{14}$ is —$CH_3$ or —$C_2H_5$.

3. A lubricant composition according to claim 2, where in the compound of formula I, R is —H, $R^1$ and $R^2$, independently of each other, are each $C_3$-$C_{12}$-alkyl, cyclohexyl, phenyl or phenyl substituted by one to three $C_1$-$C_{12}$-alkyl groups, or $R^1$ and $R^2$ together are a bifunctional radical of the formula II where n is 1, $R^3$, $R^4$, $R^5$ and $R^6$ are each —H and $R^7$ and $R^8$ are each $C_1$-$C_4$-alkyl or $C_2$-$C_3$-alkoxycarbonyl, and when b is 1, X is —$OR^9$ or —$N(R^{10})(R^{11})$ where $R^9$ is —H, $C_1$-$C_{13}$-alkyl or $C_6$-$C_9$-cyclohexyl and $R^{10}$ and $R^{11}$ are each —H, or $R^{10}$ and $R^{11}$, together with the nitrogen atom to which they are bonded, are morpholine, thiomorpholino, piperazino or 4-methylpiperazino, or when b>1, X is a polyvalent radical of the formulae —$OC_mH_{2m}O$—, (—$OC_2H_4)_2O$ or (—$OCH_2)_4C$, where m is an integer from 4 to 6.

4. A lubricant composition according to claim 1, wherein, in the compound of the formula I, X, when b=1, is —$OR^9$ or X, when b>1, is a polyvalent radical of the formulae —$OC_mH_{2m}O$—, —$OCH_2$—$C(R^{12})(R^{13})$—$CH_2O$—,

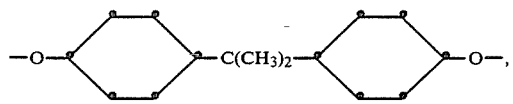

(—$OCH_2)_3C$—$R^{14}$, (—$OCH_2)_4C$ or (—$OCH_2)_3C$—$CH_2$—$O$—$CH_2$—$(CH_2O$—$)_3$, where $R^9$, $R^{12}$, $R^{13}$, $R^{14}$ and m are as defined in claim 1.

5. A lubricant composition according to claim 1, wherein, in the compound of the formula I, b is 1.

* * * * *